United States Patent

Yajima et al.

Patent Number: 5,707,646
Date of Patent: Jan. 13, 1998

[54] TASTE MASKING PHARMACEUTICAL COMPOSITION

[75] Inventors: Toshio Yajima; Kuniaki Ishii; Nobuo Umeki; Shigeru Itai; Hidefumi Hayashi; Kimihide Shimano; Ikuo Koyama, all of Tokyo, Japan

[73] Assignee: Taisho Pharmaceutical Co., Ltd., Tokyo, Japan

[21] Appl. No.: 295,672

[22] PCT Filed: Mar. 10, 1993

[86] PCT No.: PCT/JP93/00291

§ 371 Date: Sep. 9, 1994

§ 102(e) Date: Sep. 9, 1994

[87] PCT Pub. No.: WO93/17667

PCT Pub. Date: Sep. 16, 1993

[30] Foreign Application Priority Data

Mar. 12, 1992 [JP] Japan .................... 4-053442
Aug. 19, 1992 [JP] Japan .................... 4-219904

[51] Int. Cl.⁶ .......... A61K 9/10; A61K 47/32; A61K 47/02; A61K 47/44

[52] U.S. Cl. .......... 424/439; 424/458; 424/461; 424/462; 424/486; 424/487; 424/494; 424/495; 424/497; 424/501; 424/502; 424/470; 424/688; 424/691; 424/692; 514/974

[58] Field of Search .................. 424/439, 484, 424/486–487, 458, 461–462, 494, 495, 497, 688, 691–692, 501, 502, 470; 514/474

[56] References Cited

U.S. PATENT DOCUMENTS

| | | | |
|---|---|---|---|
| 3,865,935 | 2/1975 | Amann | 424/468 |
| 4,000,254 | 12/1976 | Gordon et al. | 424/497 |
| 4,340,582 | 7/1982 | Kriesel et al. | 424/480 |
| 4,695,467 | 9/1987 | Uemura et al. | 424/502 |
| 4,925,675 | 5/1990 | Giannini et al. | 424/469 |
| 5,178,878 | 1/1993 | Wehling et al. | 424/466 |
| 5,271,946 | 12/1993 | Hettche et al. | 424/502 |
| 5,494,681 | 2/1996 | Cuca et al. | 424/502 |

FOREIGN PATENT DOCUMENTS

| | | |
|---|---|---|
| 0069097 | 1/1983 | European Pat. Off. |
| 0420992 | 4/1991 | European Pat. Off. |
| 2122490 | 1/1984 | United Kingdom |

*Primary Examiner*—Edward J. Webman
*Attorney, Agent, or Firm*—Oblon, Spivak, McClelland, Maier & Neustadt, P.C.

[57] ABSTRACT

A composition for oral preparations, having a complex formed by dispersing or dissolving an unpleasantly tasting basic drug and a functional polymer compound in a substance having a low melting point, 10 to 70% by weight, based on the composition, of sugar alcohol and 0.1 to 7% by weight, based on the composition, of basic oxide. The composition for oral preparation is excellent in masking unpleasantly tasting basic drugs and has excellent performance in biological use.

9 Claims, 1 Drawing Sheet

TASTE MASKING PHARMACEUTICAL COMPOSITION

This is a national stage application under 35 U.S. 371 of Ser. No. PCT/JP93/00291, filed Mar. 10, 1993 published as WO93/17667 Sep. 16, 1993.

TECHNICAL FIELD

The present invention relates to a composition for preparations of basic drugs which taste unpleasant. More specifically, it relates to a composition for oral preparations, which is excellent in masking unpleasantly tasting basic drugs and has excellent performance in biological use.

BACKGROUND ART

There have been hitherto found a variety of methods for masking the tastes of unpleasantly tasting drugs. For example, JP-A-49-81526 discloses a method in which a macrolide is dissolved in an inert volatile organic solvent in which a coating polymer selected from the group consisting of polyvinylacetal diethylaminoacetate (hereinafter abbreviated as AEA), cellulose acetate dibutylaminohydroxypropyl ether, Eudragit® E and ethyl cellulose and at least one member selected from the group consisting of wax, higher fatty acid and salt insoluble in higher fatty acid have been dissolved or dispersed, the resultant solution is spray-dried to form coated macrolide particles, and the coated macrolides particles are recovered.

Further, as a pharmaceutical mixture for masking the taste of unpleasantly tasting basic drugs, for example, U.S. Pat. No. 4,656,027 discloses a dry powder for use as a pharmaceutical preparation, which dry powder is prepared by mixing a pharmaceutically acceptable basic substance with a bad tasting pharmaceutical which is in a form insoluble at high pH and encapsulating the mixture.

U.S. Pat. No. 4,994,260 discloses a pharmaceutical preparation for controlled release of a pharmaceutically active substance, which masks bad taste and increases stability of the pharmaceutically active substance and contains an encapsulated active substance in combination with 60 to 99% by weight of a release-controlling substance selected from the group consisting of polysaccharides, oligosaccarides, disaccharides, monosaccharides, polyhydroxy alcohols and mixtures thereof.

In known coating methods using an organic solvent such as methylene chloride, chloroform, cyclohexane, carbon tetrachloride, methyl ethyl ketone, acetone, methyl alcohol or isopropyl alcohol for dissolving a conventional coating agent, it is necessary to remove the solvent by carrying out a drying step, which requires a lot of time, many facilities, much labor and high cost and involves risks of ignition and explosion. Further, the product obtained thereby is of porous coating, and might contain a residual solvent to have a detrimental effect on a human body.

DISCLOSURE OF INVENTION

The present inventors have made an initial study on the masking of taste for overcoming the above-described problems.

At first, a study has been made of the selection of a material. As the material, which is excellent in forming a dense coating is concerned, a substance having a low melting point (wax) is available. Further, as far as a material which is readily soluble at low pH (pH 1-4, endogastric pH) and which is insoluble or hardly soluble in the mouth (pH 5-8) is concerned, a functional polymer may be taken into consideration. However, an organic solvent is required for dissolving the functional polymer, and there might be a risk concerning the toxicity and handling of the solvent. Further, since the functional polymer forms a porous coating or cannot form a dense coating, it is difficult to mask the unpleasant taste sufficiently.

Therefore, studies have been made, and it has been found that, without any organic solvent, a functional polymer can be dissolved or dispersed in a substance having a low melting point when the substance having a low melting point has been melted. It has been also found that the resultant solution or dispersion of the functional polymer can be cooled to give a dense coating and that this can be carried out safely.

Additives for enhancing the masking effect have been studied. Usual additives such as carbonates, phosphates, citrates and hydroxides cannot be said to maintain sufficient masking of taste, while specific basic oxides, particularly magnesium oxide, have an excellent effect.

It has been also found that the masking for unpleasantly tasting basic drugs is insufficient when sugar is added as an additive.

As a result, the present inventors have found a composition for preparations of unpleasantly tasting basic drugs which maintains the masking of the taste of unpleasantly tasting basic drug and has excellent bioavailability, and a process for the preparation thereof, the composition being obtained by melting a substance having a low melting point under heat at a temperature equal to or higher than the melting point thereof, dispersing or dissolving a functional polymer compound in the resultant molten substance to form a composition, melt- or heat-granulating the composition and an unpleasantly tasting basic drug to form a complex and incorporating sugar alcohol and basic oxide into the complex.

Figure 1:
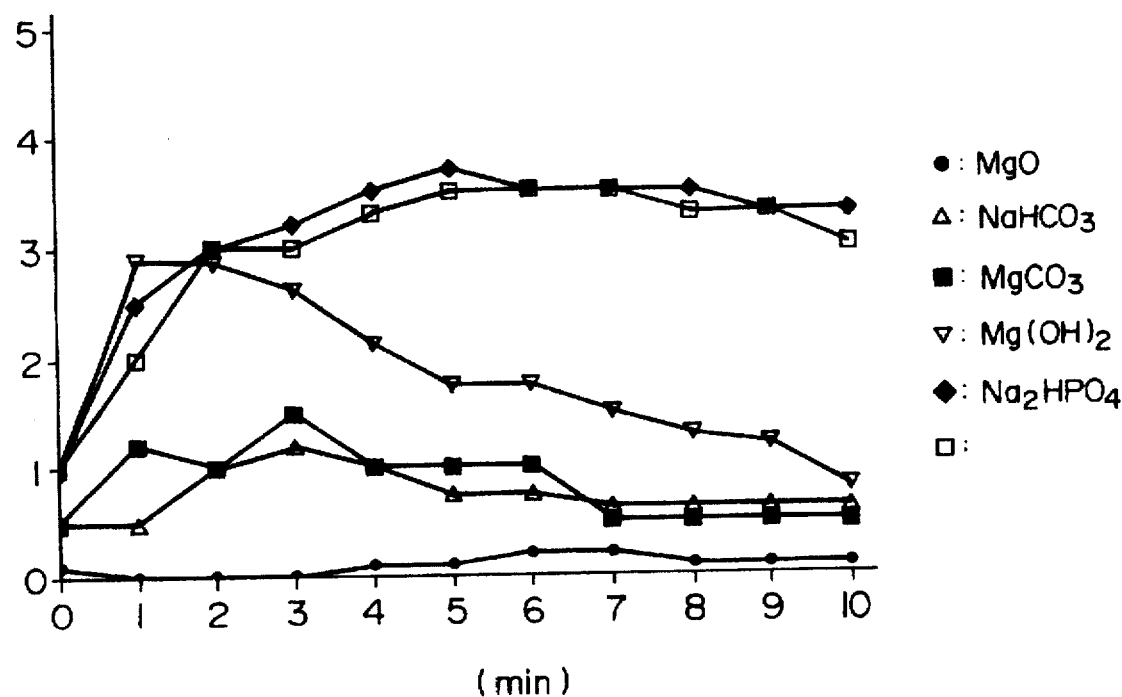
FIG. 1 is a graph showing the evaluation results on each test composition until ten minutes passed.

The total number of the points assigned by the judges was divided by the number of ten adults to obtain the bitter taste rating.

That is, the present invention provides a composition for oral preparations, which comprises a complex formed by dispersing or dissolving an unpleasantly tasting basic drug and a functional polymer compound in a substance having a low melting point, 10 to 70% by weight, based on the composition, of sugar alcohol and 0.1 to 7% by weight, based on the composition, of basic oxide.

In the present invention, the unpleasantly tasting basic drug includes unpleasantly tasting macrolides such as erythromycin, clarithromycin, kitasamycin, josamycin, midecamycin, roxithromycin and azithromycin. The amount of the unpleasantly tasting drug in the complex is 1 to 90% by weight, preferably 1 to 60% by weight.

The functional polymer compound used in the present invention includes Eudragit® E, AEA and a mixture of these.

The substance having a low melting point, used in the present invention, refers to a water-insoluble or water sparingly soluble substance having a pharmaceutically acceptable melting point of 40° to 120° C., and includes paraffin, microcrystalline wax, ceresine, hydrogenated oil, haze wax, cacao butter, myristic acid, palmitic acid, stearic acid, cetanol, stearyl alcohol, macrogol 6000, macrogol 4000, carnauba wax, bees wax, D-glucose, D-sorbitol, titanium stearate, calcium oleate, glycerin fatty acid ester, propylene glycol fatty acid ester, sorbitan fatty acid ester and mixtures of these. Preferred are glycerin monostearate, stearyl alcohol, stearic acid and mixtures of these.

The amount of the functional polymer compound in the complex is 1 to 60% by weight, particularly preferably 2 to 40% by weight. The amount of the complex in the composition for oral preparations is 20 to 60% by weight, preferably 30 to 50% by weight.

The sugar alcohol used in the present invention includes sorbitol, xylitol, mannitol, maltitol and mixtures of these. Preferred are sorbitol, mannitol, xylitol and mixtures of these.

The amount of the sugar alcohol used in the present invention based on the composition for oral preparations is 10 to 70% by weight, preferably 30 to 65% by weight.

The basic oxide used in the present invention includes magnesium oxide and aluminum oxide. Preferred is magnesium oxide. The amount of the basic oxide based on the composition for oral preparations is 0.1 to 7% by weight, preferably 0.1 to 2% by weight. The dose of magnesium oxide is not more than 70 mg.

In producing the composition for oral preparations provided by the present invention, the complex is first produced by the so-called melt-granulation method or heat-granulation method. For example, the complex can be produced by dispersing or dissolving a functional polymer compound in a substance having a low melting point which is heated to a temperature equal to or higher than its melting point, mixing an unpleasantly tasting basic drug with the resultant dispersion or solution at a high temperature and cooling the mixture.

Then, the composition for oral preparations provided by the present invention, is obtained by adding and mixing a sugar alcohol and a basic oxide to the above-obtained complex. The mixing may be carried out by a general granulating method such as fluidized bed granulation or agitating granulation. In the granulation, a solution or suspension of the basic oxide in water or a binder solution is used as a solvent for the fluidized bed granulation or agitating granulation, whereby there can be obtained a desirable composition for oral preparations. That is, the composition gives preparations in which the drug is hardly eluted from the complex.

The so-obtainable composition for oral preparations can be formed into solid oral preparations such as granules, a powder, a capsule, a tablet and dry syrup by optionally mixing it with other known additives such as an excipient, a disintegrant, a binder, a lubricant, an antioxidant, a coating agent, a colorant, a flavor, a surfactant and a plasticizer.

The excipient includes crystalline cellulose, sodium carboxymethyl cellulose, calcium hydrogenphosphate, flour starch, rice starch, corn starch, potato starch, sodium carboxylmethyl starch, dextrin, α-cyclodextrin, β-cyclodextrin, carboxyvinyl polymer, light silicic acid anhydride, titanium oxide, magnesium aluminomethasilicate, polyethylene glycol and medium chain triglyceride.

The disintegrant includes hydroxypropyl cellulose substituted in a low degree, carboxymethyl cellulose, calcium carboxymethyl cellulose, sodium carboxymethyl cellulose, cross-linked sodium carboxymethyl cellulose (Ac-Di-sol®), starch, crystalline cellulose, hydroxypropyl starch and partially alpha-formed starch.

The binder includes methyl cellulose, hydroxypropyl cellulose, hydroxylpropylmethyl cellulose, polyvinyl pyrrolidone, gelatin, gum arabic, ethyl cellulose, polyvinyl alcohol, pullulan, a-starch, agar, traganth, sodium alginate, and propylene glycol alginate ester.

The lubricant includes magnesium stearate, calcium stearate, polyoxyl stearate, cetanol, talc, hydrogenated oil, sucrose fatty acid ester, dimethyl polysiloxane, microcrystalline wax, bees wax and white beeswax.

The antioxidant includes dibutylhydroxytoluene (BHT), propyl gallate, butylhydroxyanisole (BHA), α-tocopherol and citric acid.

The coating agent includes hydroxypropylmethyl cellulose, hydroxypropyl cellulose, methyl cellulose, ethyl cellulose, hydroxypropylmethyl cellulose phthalate, hydroxypropylmethyl cellulose acetate succinate, carboxymethylethyl cellulose, acetate phthalate cellulose, polyvinylacetal diethylaminoacetate, aminoalkyl methacrylate copolymer, hydroxypropylmethyl cellulose acetate succinate, a methacrylic acid copolymer, cellulose acetate trimellitate (CAT), polyvinyl acetate phthalate and shellac.

The colorant includes tar dyestuff and titanium oxide.

The surfactant includes polyoxyethylene hardened castor oil, glycerin monostearate, sorbitan monostearate, sorbitan monopalmitate, sorbitan monolaurate, a polyoxyethylene polyoxypropylene block copolymer, polysorbates, sodium laurylsulfate, macrogols and sucrose fatty acid ester.

The plasticizer includes triethyl citrate, triacetin and cetanol.

The flavor includes menthol.

INDUSTRIAL APPLICABILITY

The composition for oral preparations, provided by the present invention, constantly masks the taste of unpleasantly tasting basic drugs and is excellent in bioavailability.

Further, the composition for oral preparations of unpleasantly tasting basic drugs, provided by the present invention, does not give unpleasant taste when suspended in water and further continuously stored at 5° C. for 3 days. Moreover, the composition of the present invention is excellent in bioavailability and gives excellent preparations as oral preparations such as syrup for infants.

BEST MODE FOR CARRYING OUT THE INVENTION

The present invention will be specifically explained hereinafter by reference to Examples and Test Examples.

EXAMPLE 1

700 Grams of stearyl alcohol was melted at about 100° C. and 100 g of Eudragit® E was dispersed and dissolved therein. Further, 200 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 20% clarithromycin complex was obtained. 90 Grams of sorbitol, 0.2 g of magnesium oxide and 9.8 g of crystalline cellulose were added to 100 g of the above complex to give a composition containing 10% of clarithromycin for oral preparations.

EXAMPLE 2

600 Grams of stearic acid was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 100 Grams of sorbitol, 100 g of xylitol, 347 g of mannitol, 50 g of maltitol and 70 g of magnesium oxide were added to 333 g of the above complex to give a composition containing 10% of clarithromycin for oral preparations.

EXAMPLE 3

600 Grams of stearyl alcohol was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 657 Grams of sorbitol and 10 g of magnesium oxide were added to 333 g of the above complex, and the resultant mixture was subjected to fluidized granulation with water to give a composition containing 10% of clarithromycin for oral preparations.

EXAMPLE 4

600 Grams of glyceryl monostearate was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 500 Grams of mannitol, 20 g of magnesium oxide, 125 g of starch, 20 g of hydroxypropyl cellulose and 2 g of carboxymethyl cellulose were added to, and homogeneously mixed with 333 g of the above complex, and the resultant mixture was subjected to fluidized granulation with water to give a composition containing 10% of clarithromycin for oral preparations.

EXAMPLE 5

600 Grams of hydrogenated oil was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 300 Grams of sorbitol, 300 g of mannitol, 10 g of sodium carboxymethyl cellulose and 47 g of crystalline cellulose were added to 333 g of the above complex. Separately, 10 g of magnesium oxide was suspended in water to prepare a binder solvent. The above-obtained mixture was subjected to fluidized granulation in the presence of the binder solvent to give a composition containing 10% of clarithromycin for oral preparations.

EXAMPLE 6

600 Grams of stearyl alcohol was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 300 Grams of sorbitol, 100 g of mannitol, 100 g of xylitol, 100 g of maltitol, 10 g of sodium carboxymethyl cellulose, 20 g of magnesium oxide, 14 g of starch, 20 g of hydroxypropyl cellulose and 3 g of saccharin sodium were added to, and homogeneously mixed with, 333 g of the above complex, and the resultant mixture was subjected to fluidized granulation in the presence of water as a granulating solvent to give a dry syrup containing 10% of clarithromycin.

EXAMPLE 7

600 Grams of glyceryl monostearate was melted at about 100° C., and 100 g of Eudragit® E was dispersed and dissolved therein. Further, 300 g of clarithromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% clarithromycin complex was obtained. 400 Grams of sorbitol, 229 g of xytitol, 10 g of sodium carboxylmethyl cellulose, 5 g of magnesium oxide, 20 g of hydroxypropyl cellulose and 3 g of saccharin sodium were added to, and homogeneously mixed with, 333 g of the above complex, and the resultant mixture was subjected to fluidized granulation in the presence of water as a granulating solvent to give a composition containing 10% of clarithromycin for oral preparations.

One gram of the above-obtained composition was suspended in about 5 ml of water to give a syrup.

EXAMPLE 8

700 Grams of stearyl alcohol was melted at about 100° C., and 100 g of Eudragit® E was dispersed and dissolved therein. Further, 200 g of erythromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 20% erythromycin complex was obtained. 90 Grams of sorbitol, 0.2 g magnesium oxide and 9.8 g of crystalline cellulose were added to 100 g of the above complex to give a composition containing 10% of erythromycin for oral preparations.

EXAMPLE 9

600 Grams of stearic acid was melted at about 100° C., and 100 g of Eudragit® E was dispersed and .dissolved herein. Further, 300 g of erythromycin was dispersed in the mixture. The resultant dispersion was spray-cooled and granulated with a spray-drying apparatus at an inlet temperature of 50° C. at a rotary disc rotation rate of 10,000 rpm. As a result, about 950 g of a 30% erythromycin complex was obtained. 100 Grams of sorbitol, 100 g of xylitol, 347 g of mannitol, 50 g of maltitol and 70 g of magnesium oxide were added to 333 g of the above complex to give a composition containing 10% erythromycin for oral preparations.

EXAMPLE 10

600 Grams of stearyl alcohol was melted at about 100° C., and 100 g of Eudragit® E was dispersed and dissolved therein. Further, 300 g of erythromycin was dispersed in the mixture. The resultant dispersion was spray cooled and granulated with a spray-drying apparatus at an inlet temperature of 50° C. at a rotary disc rotation rate of 10,000 rpm. As a result, about 950 g of a 30% erythromycin complex was obtained. 657 Grams of sorbitol and 10 g of magnesium oxide were added to 333 g of the above complex, and the resultant mixture was subjected to fluidized granulation with water to give a composition containing 10% of erythromycin for oral preparations.

EXAMPLE 11

600 Grams of hydrogenated oil was melted at about 100° C., and 100 g of Eudragit® E was dispersed and dissolved therein. Further, 300 g of erythromycin was dispersed in the mixture. The resultant dispersion was spray-cooled and granulated with a spray-drying apparatus at an inlet temperature of 50° C. at a rotary disc rotation rate of 10,000 rpm. As a result, about 950 g of a 30% erythromycin complex was obtained. 300 Grams of sorbitol, 300 g of mannitol, 10 g of sodium carboxymethyl cellulose and 47 g of crystalline cellulose were added to 333 g of the above complex. Separately, 10 g of magnesium oxide was suspended in water to prepare a binder solvent. The above-obtained mixture was subjected to fluidized granulation in the presence of the binder solvent to give a composition containing 10% of erythromycin for oral preparations.

EXAMPLE 12

600 Grams of stearyl alcohol was melted at about 100° C., and 100 g of Eudragit® E was dispersed and dissolved therein. Further, 300 g of erythromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% erythromycin complex was obtained. 300 Grams of sorbitol, 100 g of mannitol, 100 g of xylitol, 100 g of maltitol, 10 g of sodium carboxylmethyl cellulose, 20 g of magnesium oxide, 14 g of starch, 20 g of hydroxypropyl cellulose and 3 g of saccharin sodium were added to, and homogeneously mixed with, 333 g of the above complex, and the resultant mixture was subjected to fluidized granulation in the presence of water as a granulating solvent to give a dry syrup containing 10% of erythromycin.

EXAMPLE 13

600 Grams of glyceryl monostearate was melted at about 100° C., and 100 g of Eudragit® E was dispersed and dissolved therein. Further, 300 g of erythromycin was dispersed in the mixture. The resultant dispersion was spray-cooled and granulated with a spray-drying apparatus at an inlet temperature of 50° C. at a rotary disk rotation rate of 10,000 rpm. As a result, about 950 g of a 30% erythromycin complex was obtained. 400 Grams of sorbitol, 229 g of xylitol, 10 g of sodium carboxylmethyl cellulose, 5 g of magnesium oxide, 20 g of hydroxypropyl cellulose and 3 g of saccharin sodium were added to, and homogeneously mixed with, 333 g of the above complex, and the resultant mixture was subjected to fluidized granulation in the presence of water as a granulating solvent to give a composition containing 10% of erythromycin for oral preparations.

One gram of the above-obtained composition was suspended in above 5 ml of water to give a syrup.

TEST EXAMPLE 1

(Test compositions)

Composition for oral preparations, prepared in Example 3.

Compositions for oral preparations, prepared in the same manner as in Example 3 except that the magnesium oxide was replaced with the same amount of sodium hydrogen carbonate, magnesium carbonate, magnesium hydroxide, sodium dihydrogenphosphate or Neucilin®.

(Test method)

One gram of each of the test compositions was orally administered to 10 healthy adults to evaluate the bitterness of each composition. The evaluation was conducted on the basis of the following six ratings immediately after administration until 10 minutes passed.

0: Taste no bitterness
1: Taste a presence of bitterness
2: Taste bitter to some extent
3: Taste bitter
4: Taste bitter, but tolerable
5: Taste bitter intolerably (Results)

The evaluation results on each test composition by the ten adults were average, and FIG. 1 shows the results.

TEST EXAMPLE 2

(Test compositions)

Compositions for oral preparations, prepared in Examples 1 to 13.

Compositions prepared as described in the following Control Examples 1 to 10.

CONTROL EXAMPLE 1

700 Grams of stearyl alcohol was melted at about 100° C., and 300 g of clarithromycin was dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition.

CONTROL EXAMPLE 2

600 Grams of stearyl alcohol was melted at about 100° C., and 100 g of Eudragit® E was dispersed and dissolved therein. Further, 300 g of clarithromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition.

CONTROL EXAMPLE 3

600 Grams of stearyl alcohol was melted at about 100° C., and 100 g of Eudragit® E was dispersed and dissolved therein. Further, 300 g of clarithromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition. Then, 657 g of sorbitol and 10 g of crystalline cellulose were added to, and homogeneously mixed with, 333 g of the above-obtained composition, and the resultant mixture was subjected to fluidized granulation in the presence of water as a granulating solvent to give a composition containing 10% of clarithromycin.

CONTROL EXAMPLE 4

600 Grams of stearyl alcohol was melted at about 100° C., and 100 g of Eudragit® E was dispersed and dissolved therein. Further, 300 g of clarithromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition. Then, 70 g of magnesium oxide and 667 g of crystalline cellulose were added to, and homogeneously mixed with, 333 g of the above-obtained composition, and the resultant mixture was subjected to fluidized granulation in the presence of water as a granulating solvent to give a composition containing 10% of clarithromycin.

CONTROL EXAMPLE 5

600 Grams of stearyl alcohol was melted at about 100° C., and 100 g of Eudragit® E was dispersed and dissolved therein. Further, 300 g of clarithromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition. Then, 70 g of magnesium oxide, 5 g of sorbitol and 592 g of crystalline cellulose were added to, and homogeneously mixed with, 333 g of the above-obtained composition, and the resultant mixture was subjected to fluidized granulation in the presence of water as a granulating solvent to give a composition containing 10% of clarithromycin.

CONTROL EXAMPLE 6

600 Grams of stearyl alcohol was melted at about 100° C., and 100 g of Eudragit® E was dispersed and dissolved therein. Further, 300 g of clarithromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% clarithromycin composition. Then, 100 g of magnesium oxide and 567 g of sorbitol were added to, and homogeneously mixed with, 333 g of the above-obtained composition, and the resultant mixture was subjected to fluidized granulation in the presence of water as a granulating solvent to give a composition containing 10% of clarithromycin.

CONTROL EXAMPLE 7

700 Grams of stearyl alcohol was melted at about 100° C., and 100 g of Eudragit® E was dispersed and dissolved therein. Further, 300 g of erythromycin was dispersed therein. The resultant dispersion was spray-cooled and granulated with a spray-drying apparatus at an inlet temperature of 50° C. at a rotary disk rotation rate of 10,000 rpm, to give about 950 g of a 30% erythromycin composition.

CONTROL EXAMPLE 8

600 Grams of stearyl alcohol was melted at about 100° C., and 100 g of Eudragit® E was dispersed and dissolved therein. Further, 300 g of erythromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% erythromycin composition.

CONTROL EXAMPLE 9

600 Grams of stearyl alcohol was melted at about 100° C., and 100 g of Eudragit® E was dispersed and dissolved therein. Further, 300 g of erythromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% erythromycin composition. Then, 657 g of sorbitol and 10 g of crystalline cellulose were added to, and homogeneously mixed with, 333 g of the above-obtained composition, and the resultant mixture was subjected to fluidized granulation in the presence of water as a granulating solvent to give a composition containing 10% erythromycin.

CONTROL EXAMPLE 10

600 Grams of stearyl alcohol was melted at about 100° C., and 100 g of Eudragit® E was dispersed and dissolved therein. Further, 300 g of erythromycin was also dispersed therein. The resultant dispersion was spray-cooled and granulated with a spray-drying apparatus at an inlet temperature of 50° C. at a rotary disk rotation rate of 10,000 rpm, to give about 950 g of a 30% erythromycin composition. Then, 70 g of magnesium oxide and 597 g of crystalline cellulose were added to, and homogeneously mixture was subjected to fluidized granulation in the presence of water as a granulating solvent to give a composition containing 10% of erythromycin.

(Test method)

One gram of each of the test compositions was orally administered to 10 healthy adults to evaluate on the basis of the following six ratings immediately after administration until 10 minutes passed.

0: Taste no bitterness

1: Taste a presence of bitterness

2: Taste bitter to some extent

3: Taste bitter

4: Taste bitter, but tolerable

5: Taste bitter intolerably (Results)

The evaluation results on each test composition by the ten adults were averaged, and Tables 1 and 2 show the results.

TABLE 1

| | Im'ly after | 1 minute | 2 minutes | 4 minutes | 6 minutes | 8 minutes | 10 minutes |
|---|---|---|---|---|---|---|---|
| Cn Ex. 1 | 2 | 3 | 3 | 3 | 3 | 3 | 3 |
| Cn Ex. 2 | 2 | 3 | 4 | 3 | 3 | 3 | 3 |
| Cn Ex. 3 | 2 | 2 | 2 | 3 | 3 | 2 | 2 |
| Cn Ex. 4 | 1 | 2 | 2 | 2 | 2 | 2 | 2 |
| Cn Ex. 5 | 1 | 1 | 2 | 2 | 2 | 2 | 2 |
| Cn Ex. 6 | 0 | 0 | 0 | 0 | 0 | 0 | 0 |
| Ex. 1 | 0 | 0 | 0 | 0 | 0 | 0 | 0 |
| Ex. 2 | 0 | 0 | 0 | 0 | 0 | 0 | 0 |
| Ex. 3 | 0 | 0 | 0 | 0 | 0 | 0 | 0 |
| Ex. 4 | 0 | 0 | 0 | 0 | 0 | 0 | 0 |
| Ex. 5 | 0 | 0 | 0 | 0 | 0 | 0 | 0 |
| Ex. 6 | 0 | 0 | 0 | 0 | 0 | 0 | 0 |
| Ex. 7 | 0 | 0 | 0 | 0 | 0 | 0 | 0 |

Cn Ex. = Control Example, Ex. = Example

TABLE 2

| | Im'ly after | 1 minute | 2 minutes | 4 minutes | 6 minutes | 8 minutes | 10 minutes |
|---|---|---|---|---|---|---|---|
| Cn Ex. 7 | 2 | 3 | 3 | 3 | 3 | 3 | 3 |
| Cn Ex. 8 | 2 | 3 | 4 | 3 | 3 | 3 | 3 |
| Cn Ex. 9 | 2 | 2 | 2 | 3 | 3 | 2 | 2 |

TABLE 2-continued

|  | Im'ly after | 1 minute | 2 minutes | 4 minutes | 6 minutes | 8 minutes | 10 minutes |
|---|---|---|---|---|---|---|---|
| Cn Ex. 10 | 1 | 2 | 2 | 2 | 2 | 2 | 2 |
| Ex. 8 | 0 | 0 | 0 | 0 | 0 | 0 | 0 |
| Ex. 9 | 0 | 0 | 0 | 0 | 0 | 0 | 0 |
| Ex. 10 | 0 | 0 | 0 | 0 | 0 | 0 | 0 |
| Ex. 11 | 0 | 0 | 0 | 0 | 0 | 0 | 0 |
| Ex. 12 | 0 | 0 | 0 | 0 | 0 | 0 | 0 |
| Ex. 13 | 0 | 0 | 0 | 0 | 0 | 0 | 0 |

Cn Ex. = Control Example, Ex. = Example

TEST EXAMPLE 3

(Test Compositions)

Compositions for preparations, prepared in Examples 1 to 7.

Compositions prepared in Control Example 1 in Text Example 2.

(Test method)

One gram of each of the test compositions was subjected to an elution test according to Japanese Pharmacopoeia, 11th edition.

An acetic acid buffer solution having pH of 4.0 was used as an eluting solution. The paddle rotation rate was set at 100 rpm, and the test compositions were measured for elutions ratios after 10 minutes.

(Results)

Table 3 shows the elutions ratios.

TABLE 3

|  | 10 minutes |
|---|---|
| Control Example 1 | 5 |
| Example 1 | 100 |
| Example 2 | 100 |
| Example 3 | 100 |
| Example 4 | 100 |
| Example 5 | 100 |
| Example 6 | 100 |
| Example 7 | 100 |

TEST EXAMPLE 4

(Test compositions)

Compositions for preparations, prepared in Examples 1 to 7.

Compositions prepared in Control Examples 3 to 6 in Test Example 2.

(Test method)

One gram of each of the above test compositions was separately suspended in about 5 ml, and the resultant suspensions were stored in a refrigerator (5° C.) for 1 day. Then, each of the suspensions was administered to ten healthy adults to evaluate the bitterness of the compositions. The evaluation was conducted on the basis of the following six ratings immediately after administration until 10 minutes passed.

0: Taste no bitterness

1: Taste a presence of bitterness

2: Taste bitter to some extent

3: Taste bitter

4: Taste bitter, but tolerable

5: Taste bitter intolerably (Results)

The evaluation results on each test composition by the ten adults were averaged, and Table 4 shows the results.

TABLE 4

|  | Im'ly after | 1 minute | 2 minutes | 4 minutes | 6 minutes | 8 minutes | 10 minutes |
|---|---|---|---|---|---|---|---|
| Cn Ex. 3 | 4 | 4 | 5 | 5 | 5 | 5 | 5 |
| Cn Ex. 4 | 3 | 4 | 4 | 5 | 5 | 4 | 4 |
| Cn Ex. 5 | 3 | 3 | 3 | 4 | 4 | 3 | 3 |
| Cn Ex. 6 | 0 | 0 | 0 | 0 | 0 | 0 | 0 |
| Ex. 1 | 0 | 0 | 0 | 0 | 0 | 0 | 0 |
| Ex. 2 | 0 | 0 | 0 | 0 | 0 | 0 | 0 |
| Ex. 3 | 0 | 0 | 0 | 0 | 0 | 0 | 0 |
| Ex. 4 | 0 | 0 | 0 | 0 | 0 | 0 | 0 |
| Ex. 5 | 0 | 0 | 0 | 0 | 0 | 0 | 0 |
| Ex. 6 | 0 | 0 | 0 | 0 | 0 | 0 | 0 |
| Ex. 7 | 0 | 0 | 0 | 0 | 0 | 0 | 0 |

Cn Ex. = Control Example, Ex. = Example

TEST EXAMPLE 5

(Test compositions)

Composition for preparations, prepared in Example 3.

Composition prepared in Control Example 6 in Test Example 2.

(Test method)

Two grams of the composition prepared in Example 3 and the composition prepared in Control Example 6 were administered to six healthy adults according to a crossover method, and they were measured for concentrations in the blood to determine AUC and Cmax. Table 5 shows the results.

TABLE 5

|  | AUC (µg · hr/ml) | Cmax (µg/ml) |
|---|---|---|
| Example 3 | 8 | 1.3 |
| Control Example 6 | 4 | 0.5 |

We claim:

1. A composition for oral preparations, which comprises:
   a) a complex formed by dispersing or dissolving an unpleasantly tasting basic drug and a functional polymer compound in a substance having a melting point of 40° to 120° C., wherein the functional polymer compound is selected from the group consisting of Eudragit® E, AEA (polyvinylacetal diethylaminoacetate) and mixtures thereof,
   b) 10 to 70% by weight, based on the composition, of sugar alcohol, and
   c) 0.1 to 7% by weight, based on the composition, of basic oxide.

2. A composition according to claim 1, wherein the complex is obtained by melt- or heat-granulating a functional polymer compound dispersed or dissolved in a heat-melted substance having a melting point of 40° to 120° C. and a basic drug.

3. A composition according to claim 1, wherein the functional polymer compound is contained in an amount of 1 to 60% by weight based on the complex.

4. A composition according to claim 1, wherein the basic drug is one of unpleasantly tasting macrolides.

5. A composition according to claim 1, wherein the substance having a low melting point is a pharmaceutically acceptable substance having a melting point of 40° to 120° C. and being insoluble or sparingly soluble in water.

6. A composition according to claim 1, wherein the basic oxide is magnesium oxide.

7. A composition according to claim 1, which has a form of dry syrup.

8. A composition according to claim 1, wherein the basic oxide is selected from the group consisting of magnesium oxide and aluminum oxide.

9. The composition of claim 8, wherein the functional polymer is Eudragit® E (methyl methacrylate-butyl methacrylate-dimethylaminoethyl methacrylate copolymer).

* * * * *